US011538160B2

(12) United States Patent
Yao et al.

(10) Patent No.: US 11,538,160 B2
(45) Date of Patent: Dec. 27, 2022

(54) SYSTEMS AND METHODS FOR SCATTER CORRECTION OF IMAGE

(71) Applicant: SHANGHAI UNITED IMAGING HEALTHCARE CO., LTD., Shanghai (CN)

(72) Inventors: Peng Yao, Shanghai (CN); Zhou Yuan, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 169 days.

(21) Appl. No.: 16/914,538

(22) Filed: Jun. 29, 2020

(65) Prior Publication Data
US 2020/0327672 A1 Oct. 15, 2020

Related U.S. Application Data

(63) Continuation of application No. PCT/CN2018/121049, filed on Dec. 14, 2018.

(30) Foreign Application Priority Data

Dec. 29, 2017 (CN) .................... 201711489052.X
Dec. 29, 2017 (CN) .................... 201711489188.0

(51) Int. Cl.
*G06K 9/00* (2022.01)
*G06T 7/00* (2017.01)
(Continued)

(52) U.S. Cl.
CPC .......... *G06T 7/0014* (2013.01); *A61B 6/5282* (2013.01); *A61B 6/583* (2013.01);
(Continued)

(58) Field of Classification Search
CPC ..... G06T 7/10–194; G06T 2207/20112; G06T 2207/10072–10128; G06T 7/60–80;
(Continued)

(56) References Cited

U.S. PATENT DOCUMENTS 6,256,367 B1    7/2001  Vartanian
2003/0072409 A1  4/2003  Kaufhold et al.
(Continued)

FOREIGN PATENT DOCUMENTS

CN    101158653 A    4/2008
CN    101566590 A    10/2009
(Continued)

OTHER PUBLICATIONS

D, McLean et al., Scatter-to-Primary Ratio and Absorption Efficiency in Screen-Film and Computed Radiography Systems, European Journal of Radiology, 21(3): 212-216, 1996.
(Continued)

*Primary Examiner* — Atiba O Fitzpatrick
(74) *Attorney, Agent, or Firm* — Metis IP LLC

(57) ABSTRACT

The present disclosure is related to a method for scattering correction of an image. The method may include obtaining an image of a subject and a reference image of air. The method may also include identifying an OOI from the image, the OOI including one or more pixels. For each pixel of the one or more pixels of the OOI, the method may also include determining an equivalent thickness of the OOI corresponding to the each pixel based on a pixel value of the each pixel and the reference image, and determining a scatter correction coefficient of the each pixel based at least in part on the equivalent thickness of the OOI corresponding to the each pixel. The method may further include correcting
(Continued)

the pixel value of the each pixel using the corresponding scatter correction coefficient for each pixel of the one or more pixels of the OOI.

10 Claims, 9 Drawing Sheets

(51) Int. Cl.
    *G06T 7/174*     (2017.01)
    *A61B 6/00*     (2006.01)
    *G06T 7/60*     (2017.01)
    *G06T 11/00*     (2006.01)
(52) U.S. Cl.
    CPC ............ *G06T 7/174* (2017.01); *G06T 7/60* (2013.01); *G06T 11/008* (2013.01); *G06T 2207/10116* (2013.01); *G06T 2207/30168* (2013.01)
(58) Field of Classification Search
    CPC ......... G06T 11/008; G06T 2207/30168; G06T 7/0012–0016; G06T 2207/30004–30104; G06T 7/0014; G06T 7/174; G06T 2207/10116; A61B 5/7485; A61B 6/5282; A61B 6/583; A61B 6/584; A61B 8/587; A61B 2017/00707; G06V 20/695; G06V 40/162; G06V 2201/03; G06K 9/6224; G01N 2223/05; G01N 2223/051; G01N 2223/053; G01N 2223/063; G16H 50/20
    See application file for complete search history.

(56) References Cited

U.S. PATENT DOCUMENTS

| | | |
|---|---|---|
| 2005/0063518 A1 | 3/2005 | Nukui |
| 2008/0013673 A1 | 1/2008 | Ruhmschopf |
| 2008/0253515 A1 | 10/2008 | Bertram et al. |
| 2009/0046829 A1 | 2/2009 | Schweizer et al. |
| 2009/0092221 A1 | 4/2009 | Manabe et al. |
| 2010/0189376 A1 | 7/2010 | Bertram et al. |
| 2011/0164722 A1* | 7/2011 | Wiegert ............... G06T 11/005 378/7 |
| 2014/0018671 A1 | 1/2014 | Li et al. |
| 2014/0328452 A1 | 11/2014 | Tsubota et al. |
| 2016/0086328 A1* | 3/2016 | Enomoto ............... G06T 11/60 382/132 |
| 2020/0375566 A1* | 12/2020 | Ohno ..................... G06T 5/001 |

FOREIGN PATENT DOCUMENTS

| | | |
|---|---|---|
| CN | 104616251 A | 5/2015 |
| CN | 104840211 A | 8/2015 |
| CN | 106485680 A | 3/2017 |
| CN | 107202805 A | 9/2017 |
| CN | 107802280 A | 3/2018 |
| CN | 107928690 A | 4/2018 |
| CN | 108335269 A | 7/2018 |
| CN | 108577872 A | 9/2018 |

OTHER PUBLICATIONS

Gustaf Ullman et al., Distributions of Scatter-to-Primary and Signal-to-Noise Ratios Per Pixel in Digital Chest Imaging, Radiation Protection Dosimetry, 114(1-3): 355-358, 2005.
Simon Cardoso et al., Evaluation of Scatter-to-Primary Ratio in Radiological Conditions, Applied Radiation and Isotopes, 67(4): 544-548, 2009.
Risto Miettunen et al., The Scatter-to-Primary Ratio as a Function of Varying X-Ray Absorption Measured by Computed Radiography, European Journal of Radiology, 13(2): 156-159, 1991.
The Extended European Search Report in European Application No. 18896349.0 dated Dec. 17, 2020, 8 pages.
International Search Report in PCT/CN2018/121049 dated Feb. 27, 2019, 4 pages.
Written Opinion in PCT/CN2018/121049 dated Feb. 27, 2019, 5 pages.

* cited by examiner

700

> Obtaining a correction template that corresponds to a target equivalent thickness, the target equivalent thickness being the equivalent thickness of the OOI corresponding to the pixel, the correction template including a plurality of scatter correction coefficients corresponding to a plurality of detector units of the X-ray imaging device  ~710

> Designating the scatter correction coefficient of the detector unit acquiring a portion of the scan data that corresponds to the pixel as the scatter correction coefficient of the pixel  ~720

Obtaining photon information related to a plurality of photons that are detected by the plurality of detector units of the X-ray imaging device during a scan of a phantom, the phantom having a thickness being substantially equal to the equivalent thickness of the OOI corresponding to the pixel, the phantom having an attenuation characteristic being substantially equal to an attenuation characteristic of the OOI, the photon information including an incidence angle of each of the plurality of photons on the plurality of detector units and a photon energy of each of the plurality of photons ~810

Identifying, based on the photon information, one or more scattered photons among the plurality of photons ~820

Determining, based on the photon information and the identified one or more scattered photons, the plurality of scatter correction coefficients corresponding to the plurality of detector units ~830

Obtaining photon information related to a plurality of scans, each of the plurality of scans being performed on a phantom under an imaging condition, the photon information of a scan being related to a plurality of photons detected by a plurality of detector units of an X-ray imaging device during the scan of the corresponding phantom, the photon information including an incidence angle of each of the plurality of photons on the plurality of detector units and a photon energy of each of the plurality of photons ~910

For each of the plurality of scans, identifying one or more scattered photons among the corresponding plurality of photons detected by the plurality of detector units of the X-ray imaging device based on the corresponding photon information ~920

For each of the plurality of scans, determining a candidate correction template corresponding to the imaging condition under which the scan is performed, the candidate correction template including a plurality of scatter correction coefficients each of which corresponds to each of the plurality of detector units based on the corresponding photon information and the corresponding scattered photons ~930

FIG. 9

SYSTEMS AND METHODS FOR SCATTER CORRECTION OF IMAGE

CROSS-REFERENCE TO RELATED APPLICATION

This application is a continuation of International Application No. PCT/CN2018/121049, filed on Dec. 14, 2018, which claims priority to Chinese Patent Application No. 201711489052.X, filed on Dec. 29, 2017 and Chinese Patent Application No. 201711489188.0, filed on Dec. 29, 2017. Each of the above-referenced applications is expressly incorporated herein by reference in their entireties.

TECHNICAL FIELD

The present disclosure generally relates to image processing, and more particularly, to systems and methods for scatter correction of an image.

BACKGROUND

High-energy rays (e.g., X-rays, γ-rays) are widely used in medical imaging. For example, X-rays are used in, for example, computed tomography (CT) devices or digital radiography (DR) devices to generate an image of a subject. During a scan performed by an imaging device, X-rays irradiated on the subject can pass through the subject and are detected by one or more detectors. However, some X-rays may scatter when passing through the subject, which may cause scatter noise in the image generated based on the scan. Conventionally, a grid may be assembled on the imaging device to limit the scattered X-rays from reaching the detector(s) during the scan. However, only a portion of the scattered X-rays may be limited by the grid. In addition, primary X-rays may also be limited by the grid, which may reduce the imaging quality. To improve the imaging quality, the radiation dose of the scan may need to be increased and the subject may suffer from unnecessary radiations. Thus, it is desirable to provide mechanisms for correcting an image to reduce or eliminate scatter noise in the image to improve the imaging quality and avoid unnecessary radiations on the scanned subject.

SUMMARY

In one aspect of the present disclosure, a system is provided. The system may include at least one storage device including a set of instructions for scatter correction of an image and at least one processor configured to communicate with the at least one storage device. When executing the set of instructions, the at least one processor is configured to direct the system to obtain an image of a subject and a reference image of air. The image of a subject may be generated according to scan data of the subject acquired by an X-ray imaging device. The reference image may be generated according to scan data of air acquired by the X-ray imaging device. The at least one processor may be also directed to identify an object of interest (OOI) from the image, the OOI including one or more pixels. For each pixel of the one or more pixels of the OOI, The at least one processor may be also directed to determine an equivalent thickness of the OOI corresponding to the each pixel based on a pixel value of the each pixel and the reference image, and determine a scatter correction coefficient of the each pixel based at least in part on the equivalent thickness of the OOI corresponding to the each pixel. The at least one processor may be further directed to correct the pixel value of the each pixel using the corresponding scatter correction coefficient.

In some embodiments, for each candidate pixel of one or more candidate pixels in the OOI, to determine the equivalent thickness of the OOI corresponding to the each pixel, the at least one processor may be configured to direct the system to determine a thickness of the OOI corresponding to the each candidate pixel based on a pixel value of the each candidate pixel and the reference image. The at least one processor may be further configured to direct the system to determine an average thickness of the OOI corresponding to the one or more candidate pixels based on the thicknesses of the OOI corresponding to the one or more candidate pixels. The at least one processor may be further directed to designate the average thickness of the OOI corresponding to the one or more candidate pixels as the equivalent thickness of the OOI corresponding to the each pixel.

In some embodiments, to determine a thickness of the OOI corresponding to the each candidate pixel based on a pixel value of the each candidate pixel and the reference image, the at least one processor may be further configured to direct the system to determine a ratio of the pixel value the each candidate pixel in the image of the subject to a pixel value of a pixel in the reference image corresponding the each candidate pixel, and determine the thickness of the OOI corresponding to the each candidate pixel based on the ratio and a linear attenuation coefficient of the OOI.

In some embodiments, to determine the equivalent thickness of the OOI corresponding to the each pixel, the at least one processor may be configured to direct the system to identify the OOI into a plurality of sub-areas. For each of the sub-areas, the at least one processor may be also configured to direct the system to determine a thickness of the OOI corresponding to the each candidate pixel based on a pixel value of the each candidate pixel and the reference image, and determine an average thickness of the sub-area corresponding to the one or more candidate pixels in the sub-area based on the thicknesses of the OOI corresponding to the one or more candidate pixels in the sub-area for each candidate pixel of one or more candidate pixels in the sub-area. The at least one processor may be further configured to direct the system to designate the average thickness of the sub-area corresponding to the one or more candidate pixels in the sub-area as the equivalent thickness of the OOI corresponding to each pixel in the sub-area.

In some embodiments, for each pixel of the one or more pixels of the OOI, to determine a scatter correction coefficient of the each pixel based at least in part on the equivalent thickness of the OOI corresponding to the each pixel, the at least one processor may be configured to direct the system to obtain a correction template that corresponds to a target equivalent thickness. The target equivalent thickness may be the equivalent thickness of the OOI corresponding to the each pixel. The correction template may include a plurality of scatter correction coefficients corresponding to a plurality of detector units of the X-ray imaging device. The at least one processor may be also configured to direct the system to designate the scatter correction coefficient of the detector unit acquiring a portion of the scan data that corresponds to the each pixel as the scatter correction coefficient of the each pixel.

In some embodiments, the correction template that corresponds to the target equivalent thickness may be generated according to a correction template generation process. The at least one processor may be configured to direct the system to obtain photon information related to a scan of a phantom.

The photon information may be related to a plurality of photons that are detected by the plurality of detector units of the X-ray imaging device during the scan. The phantom may have thickness being substantially equal to the target equivalent thickness and an attenuation characteristic being substantially equal to an attenuation characteristic of the OOI. The photon information may include an incidence angle of each of the plurality of photons on the plurality of detector units and a photon energy of each of the plurality of photons. The at least one processor may be also configured to direct the system to identify one or more scattered photons among the plurality of photons based on the photon information. The at least one processor may be further configured to direct the system to determine the plurality of scatter correction coefficients corresponding to the plurality of detector units based on the photon information and the identified one or more scattered photons.

In some embodiments, the correction template corresponding to the target equivalent thickness may be generated according to a Monte-Carlo simulation technique.

In some embodiments, the scan data of the subject may be acquired by the X-ray imaging device under a target imaging condition, and to obtain a correction template corresponding to the target equivalent thickness, the at least one processor may be configured to direct the system to obtain a plurality of candidate correction templates corresponding to the target equivalent thickness, each of the candidate correction templates corresponding to an imaging condition. The at least one processor may be also configured to direct the system to select the candidate correction template corresponding to the target imaging condition as the correction template corresponding to the target equivalent thickness among the plurality of candidate correction templates.

In some embodiments, the at least one processor may be configured to direct the system to identify a plurality of OOIs from the image. Each of the OOI may include one or more pixels. For each OOI of the plurality of OOIs, the at least one processor may be configured to direct the system to determine an equivalent thickness of the each OOI corresponding to each pixel in the each OOI based on a pixel value of the each pixel in the each OOI and the reference image, and determine a scatter correction coefficient of the each pixel in the each OOI based at least in part on the equivalent thickness of the each OOI corresponding to the each pixel in the each OOI. The at least one processor may be also configured to direct the system to correct the pixel value of the each pixel in the each OOI using the corresponding scatter correction coefficient. The at least one processor may be further configured to direct the system to generate a corrected image by combining the plurality of corrected OOIs.

In some embodiments, a scatter correction coefficient may include at least one of a scatter-to-primary ratio (SPR), a scatter ratio, or a primary ratio.

In some embodiments, the OOI may include at least one of an organ or a tissue of the subject.

In another aspect of the present disclosure, a system is provided. The system may include at least one storage device including a set of instructions for scatter correction of an image and at least one processor configured to communicate with the at least one storage device. When executing the set of instructions, the at least one processor may be configured to direct the system to obtain photon information related to a plurality of scans, each of the plurality of scans being performed on a phantom under an imaging condition. The photon information of a scan being related to a plurality of photons may be detected by a plurality of detector units of an X-ray imaging device during the scan of the corresponding phantom. The photon information may include an incidence angle of each of the plurality of photons on the plurality of detector units and a photon energy of each of the plurality of photons. For each of the plurality of scans, the at least one processor may be also configured to direct the system to identify one or more scattered photons among the corresponding plurality of photons detected by the plurality of detector units of the X-ray imaging device based on the corresponding photon information. For each of the plurality of scans, the at least one processor may be also configured to direct the system to determine a candidate correction template corresponding to the imaging condition under which the scan is performed, the candidate correction template including a plurality of scatter correction coefficients each of which corresponds to each of the plurality of detector units based on the corresponding photon information and the corresponding scattered photons.

In some embodiments, the at least one processor may be configured to direct the system to obtain an image of a subject. The image may be generated according to scan data of the subject acquired by the X-ray imaging device under a target imaging condition. The at least one processor may be also configured to direct the system to select the correction template corresponding to the target imaging condition among the plurality of candidate correction templates corresponding to the imaging conditions. The at least one processor may be further configured to direct the system to correct at least a portion of the image using the correction template corresponding to the target imaging condition.

In some embodiments, to correct at least a portion of the image using the correction template corresponding to the target imaging condition, the at least one processor may be configured to direct the system to identify a scatter correction coefficient of the detector unit acquiring a portion of the scan data that corresponds to the at least one pixel from the correction template corresponding to the target imaging condition for at least one pixel in the image. The at least one processor may be also configured to direct the system to correct a pixel value of the at least one pixel using the identified scatter correction coefficient for at least one pixel in the image.

In some embodiments, each of the plurality of scans may be performed on the corresponding phantom having a thickness, and the at least one processor may be configured to direct the system to obtain an image of a subject and a reference image of air. The image of a subject may be generated according to scan data of the subject acquired by the X-ray imaging device under a target imaging condition. The reference image may be generated according to scan data of air acquired by the X-ray imaging device under the target imaging condition. The at least one processor may be also configured to direct the system to identify an OOI from the image, the OOI including one or more pixels. For each pixel of the one or more pixels in the OOI, the at least one processor may be also configured to direct the system to determine an equivalent thickness of the OOI corresponding to the each pixel for each pixel of the one or more pixels in the OOI based on a pixel value of the each pixel and the reference image. For each pixel of the one or more pixels in the OOI, the at least one processor may be also configured to direct the system to select, among the plurality of candidate correction templates corresponding to the imaging conditions, a correction template that may correspond to the target imaging condition and be generated according to the scan of the phantom that may have a thickness being substantially equal to the equivalent thickness of the OOI corresponding to the each pixel. The at least one processor may be further configured to direct the system to correct the pixel value of the each pixel using the corresponding correction template for each pixel of the one or more pixels in the OOI.

In some embodiments, to correct the pixel value of the each pixel using the corresponding correction template, the at least one processor may be configured to direct the system to identify a scatter correction coefficient of the detector unit acquiring a portion of the scan data that corresponds to the each pixel from the corresponding correction template. The at least one processor may be also configured to direct the system to correct the pixel value of the each pixel using the identified scatter correction coefficient.

In another aspect of the present disclosure, a method is provided. The method may be implemented on a computing device having one or more processors and one or more storage media. The method may include obtaining an image of a subject and a reference image of air. The image of a subject may be generated according to scan data of the subject acquired by an X-ray imaging device. The reference image being generated according to scan data of air acquired by the X-ray imaging device. The method may also include identifying an OOI from the image, the OOI including one or more pixels. For each pixel of the one or more pixels of the OOI, the method may also include determining an equivalent thickness of the OOI corresponding to the each pixel based on a pixel value of the each pixel and the reference image, and determining a scatter correction coefficient of the each pixel based at least in part on the equivalent thickness of the OOI corresponding to the each pixel. The method may further include correcting the pixel value of the each pixel using the corresponding scatter correction coefficient for each pixel of the one or more pixels of the OOI.

In another aspect of the present disclosure, a method is provided. The method may be implemented on a computing device having one or more processors and one or more storage media. The method may include obtaining photon information related to a plurality of scans. Each of the plurality of scans may be performed on a phantom under an imaging condition. The photon information of a scan may be related to a plurality of photons detected by a plurality of detector units of an X-ray imaging device during the scan of the corresponding phantom. The photon information may include an incidence angle of each of the plurality of photons on the plurality of detector units and a photon energy of each of the plurality of photons. The method may also include identifying one or more scattered photons among the corresponding plurality of photons detected by the plurality of detector units of the X-ray imaging device based on the corresponding photon information for each of the plurality of scans by the X-ray imaging device. The method may also include determining a candidate correction template corresponding to the imaging condition under which the scan is performed based on the corresponding photon information and the corresponding scattered photons for each of the plurality of scans by the X-ray imaging device. The candidate correction template may include a plurality of scatter correction coefficients each of which corresponds to each of the plurality of detector units.

In another aspect of the present disclosure, a non-transitory computer-readable storage medium embodying a computer program product is provided. The non-transitory computer-readable storage medium may store instructions. When executed by at least one processor of a system, the non-transitory computer-readable storage medium may cause the system to perform a method. The method may include obtaining an image of a subject and a reference image of air. The image may be generated according to scan data of the subject acquired by an X-ray imaging device. The reference image of air may be generated according to scan data of air acquired by the X-ray imaging device. The method may also include identifying an OOI from the image, the OOI including one or more pixels. For each pixel of the one or more pixels of the OOI, the method may also include determining an equivalent thickness of the OOI corresponding to the each pixel based on a pixel value of the each pixel and the reference image, and determine a scatter correction coefficient of the each pixel based at least in part on the equivalent thickness of the OOI corresponding to the each pixel. The method may further include correcting the pixel value of the each pixel using the corresponding scatter correction coefficient for each pixel of the one or more pixels of the OOI.

In another aspect of the present disclosure, a non-transitory computer-readable storage medium embodying a computer program product is provided. The non-transitory computer-readable storage medium may store instructions. When executed by at least one processor of a system, the non-transitory computer-readable storage medium cause the system to perform a method. The method may include obtaining photon information related to a plurality of scans. Each of the plurality of scans may be performed on a phantom under an imaging condition, the photon information of a scan being related to a plurality of photons detected by a plurality of detector units of an X-ray imaging device during the scan of the corresponding phantom. The photon information may include an incidence angle of each of the plurality of photons on the plurality of detector units and a photon energy of each of the plurality of photons. The method may also include identifying, based on the corresponding photon information, one or more scattered photons among the corresponding plurality of photons detected by the plurality of detector units of the X-ray imaging device for each of the plurality of scans by the X-ray imaging device. The method may further determining a candidate correction template corresponding to the imaging condition under which the scan may be performed based on the corresponding photon information and the corresponding scattered photons for each of the plurality of scans by the X-ray imaging device. The candidate correction template may include a plurality of scatter correction coefficients each of which corresponds to each of the plurality of detector units.

In another aspect of the present disclosure, a system is provided. The system may include at least one storage device including a set of instructions for scatter correction of an image and at least one processor configured to communicate with the at least one storage device. When executing the set of instructions, the at least one processor may be configured to direct the system to obtain an image of a subject and a plurality of candidate correction templates corresponding to a plurality of imaging conditions. The image may be generated according to scan data of the subject acquired by an X-ray imaging device under a target imaging condition. Each of the plurality of candidate correction templates may include a plurality of scatter correction coefficients corresponding to a plurality of detector units of the X-ray imaging device. The at least one processor may be also configured to direct the system to select the correction template corresponding to the target imaging condition among the plurality of candidate correction templates. The at least one processor may be also configured to direct the system to correct at least a portion of the image using at least one scatter correction coefficient of the plurality of scatter correction coefficients in the correction template corresponding to the target correction template.

In some embodiments, the X-ray imaging device may be operated without a grid during acquiring the scan data of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 7 is a flowchart illustrating an exemplary process for an exemplary process for determining a scatter correction coefficient of a pixel according to some embodiments of the present disclosure;

FIG. 8 is a flowchart illustrating an exemplary process for generating a correction template corresponding to a target equivalent thickness according to some embodiments of the present disclosure; and FIG. 9 is a flowchart illustrating an exemplary process for determining a plurality of correction templates corresponding to different imaging conditions according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Figure 2:
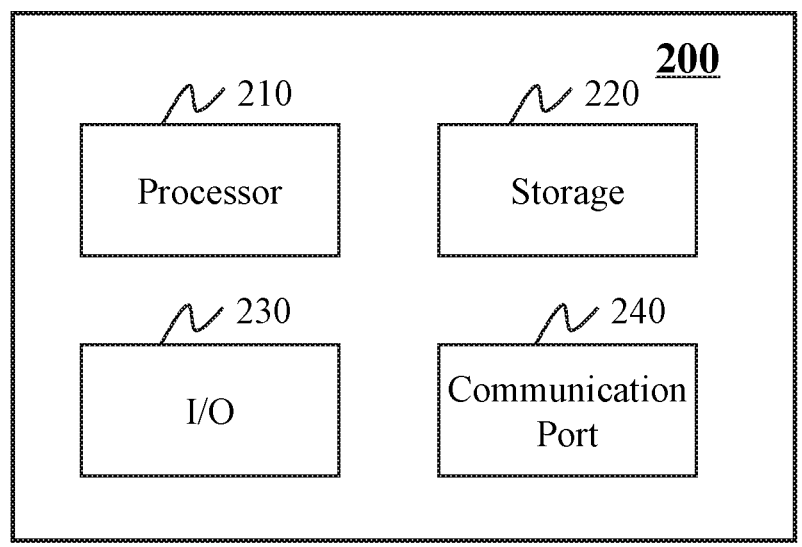
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. When a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

An aspect of the present disclosure relates to systems and methods for scatter correction of an image of a subject. The image of the subject may be generated according to scan data of the subject acquired by an X-ray imaging device. During the scan of the subject, the attenuation of X-ray photons passing through the subject (or a portion thereof) may be affect by various factors, such as the attenuation characteristic(s) of the subject (or the portion thereof) passed by the X-ray photons, and/or the traveling distance of X-ray photons. These factors may need to be considered to provide a more efficient way of scatter correction. To this end, the systems and methods may obtain a reference image of air, which is generated according to scan data of air acquired by the X-ray imaging device. The systems and methods may further identify an OOI, such as an organ and/or tissue from the image. For each pixel of the OOI, the systems and methods may determine an equivalent thickness of the OOI corresponding to the pixel, and determine a scatter correction coefficient of the pixel based at least in part on the equivalent thickness of the OOI corresponding to the pixel. The systems and methods may then correct the pixel value of each pixel of the OOI using the corresponding scatter correction coefficient. Compared with the conventional way, the systems and methods disclosed in the present disclosure may be implemented without a grid and/or without increasing the radiation dose. This may reduce the equipment cost, reduce or eliminate scatter noise of the image, improve the imaging quality, and avoid unnecessary radiations on the scanned subject.

Figure 1:
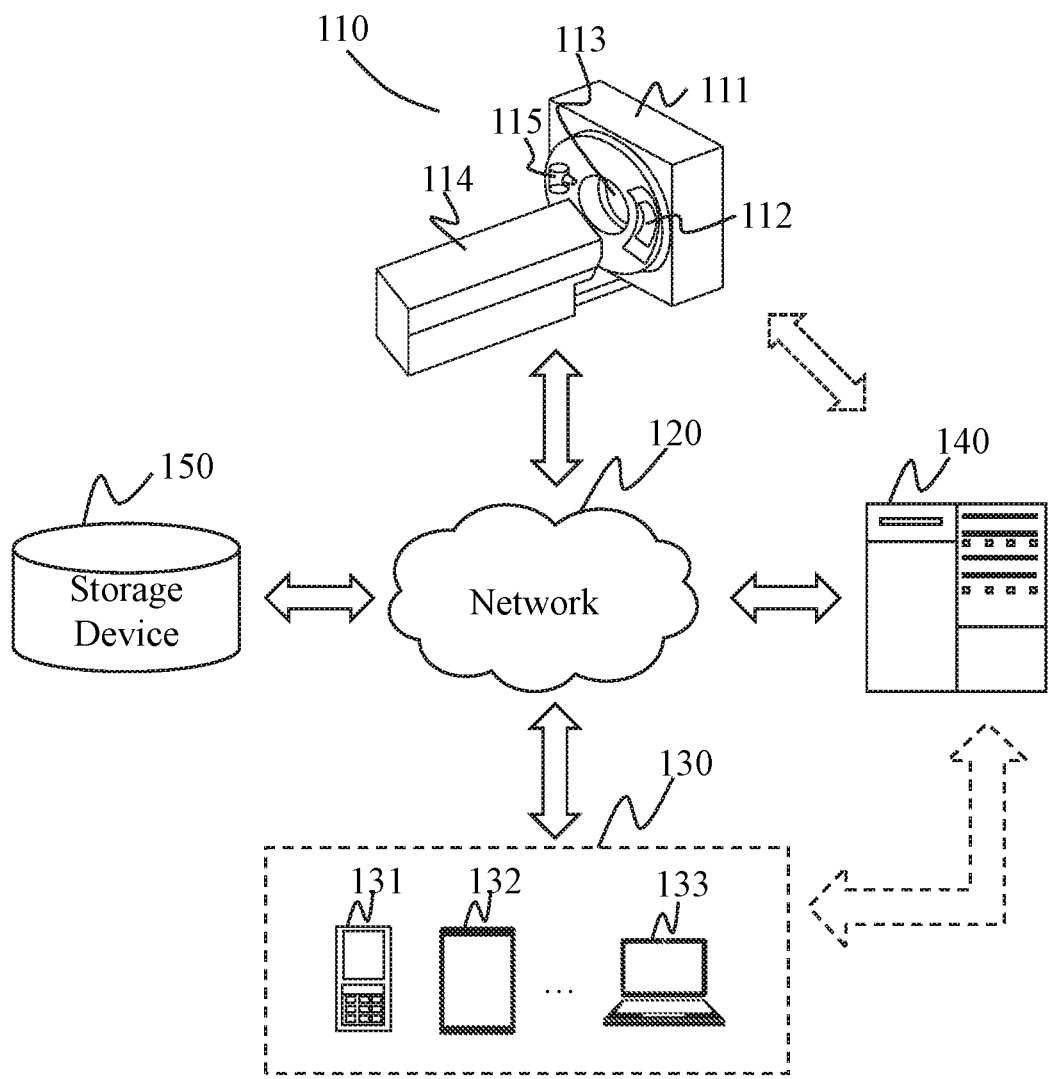
FIG. 1 is a schematic diagram illustrating an exemplary X-ray imaging system according to some embodiments of the present disclosure.

FIG. 1 is schematic diagram illustrating an exemplary X-ray imaging system according to some embodiments of the present disclosure. As shown, the X-ray imaging system 100 may include an X-ray imaging device 110, a network 120, one or more terminals 130, a processing device 140, and a storage device 150. The connection between the components in the X-ray imaging system 100 may be variable. Merely by way of example, as illustrated in FIG. 1, the X-ray imaging device 110 may be connected to the processing device 140 through the network 120. As another example, the X-ray imaging device 110 may be connected to the processing device 140 directly as indicated by the bi-directional arrow in dotted lines linking the X-ray imaging device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

The X-ray imaging device 110 may be configured to scan a subject using X-rays to collect scan data related to the subject. The scan data may be used to generate one or more images of the subject. In some embodiments, the X-ray imaging device 110 may include a computed tomography (CT) scanner, a digital radiography (DR) scanner (e.g., a mobile digital radiography), a digital subtraction angiography (DSA) scanner, a dynamic spatial reconstruction (DSR) scanner, an X-ray microscopy scanner, a multimodality scanner, or the like, or a combination thereof. Exemplary multi-modality scanners may include a computed tomography-positron emission tomography (CT-PET) scanner, a computed tomography-magnetic resonance imaging (CT-MRI) scanner, etc. The subject may be biological or non-biological. Merely by way of example, the subject may include a patient, a man-made object (e.g., a phantom), etc. As another example, the subject may include a specific portion, organ, and/or tissue of a patient.

As shown in FIG. 1, the X-ray imaging device 110 may include a gantry 111, a detector 112, a detecting region 113, a table 114, and a radiation source 115. The gantry 111 may support the detector 112 and the radiation source 115. A subject may be placed on the table 114 for scanning. The radiation source 115 may emit radioactive rays to the subject. The detector 112 may detect radiation rays (e.g., X-rays) emitted from the detecting region 113. In some embodiments, the detector 112 may include one or more detector units. The detector units may include a scintillation detector (e.g., a cesium iodide detector), a gas detector, etc. The detector unit may be include a single-row detector and/or a multi-rows detector.

The network 120 may include any suitable network that can facilitate exchange of information and/or data for the X-ray imaging system 100. In some embodiments, one or more components of the X-ray imaging system 100 (e.g., the X-ray imaging device 110, the terminal 130, the processing device 140, the storage device 150) may communicate information and/or data with each other via the network 120. For example, the processing device 140 may obtain image data from the X-ray imaging device 110 via the network 120. As another example, the processing device 140 may obtain user instructions from the terminal 130 via the network 120.

The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the X-ray imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass", an Oculus Rift", a Hololens™, a Gear VR™ etc. In some embodiments, the terminal(s) 130 may be part of the processing device 140.

Figure 3:
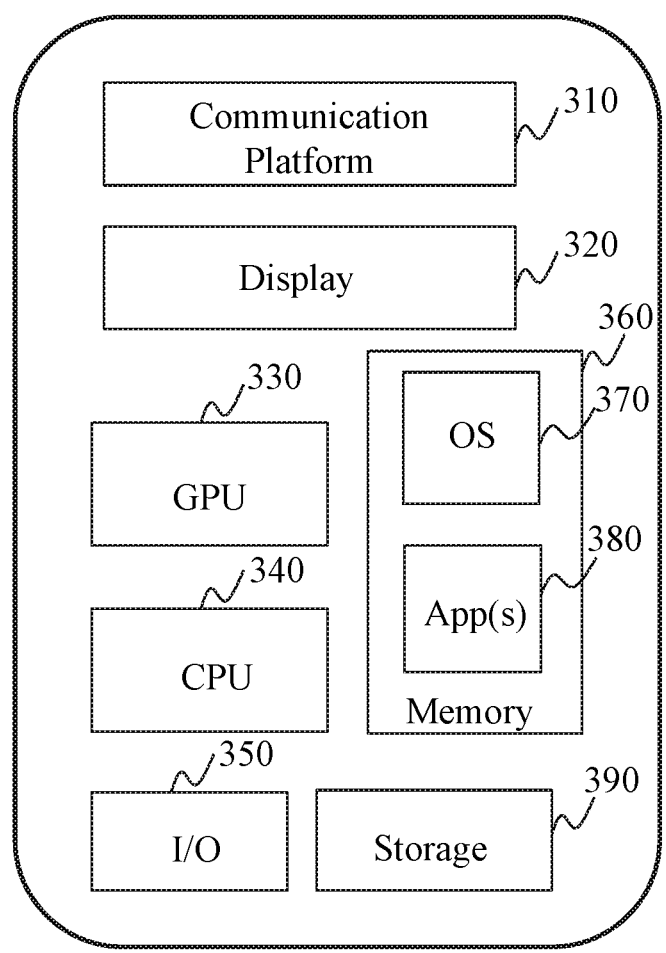
FIG. 3 is a schematic diagram illustrating exemplary hardware and/or software components of an exemplary mobile device according to some embodiments of the present disclosure.

The processing device 140 may process data and/or information obtained from the X-ray imaging device 110, the terminal 130, and/or the storage device 150. For example, the processing device 140 may perform a scatter correction on an image. In some embodiments, the processing device 140 may be a single server or a server group. The server group may be centralized or distributed. In some embodiments, the processing device 140 may be local or remote. For example, the processing device 140 may access information and/or data stored in the X-ray imaging device 110, the terminal 130, and/or the storage device 150 via the network 120. As another example, the processing device 140 may be directly connected to the X-ray imaging device 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2 or a mobile device 300 having one or more components as illustrated in FIG. 3.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage device may include a magnetic disk, an optical disk, a solid-state drive, etc. Exemplary removable storage device may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the X-ray imaging system 100 (e.g., the processing device 140, the terminal 130). One or more components in the X-ray imaging system 100 may access the data or instructions stored in the storage device 150 via the network 120. In some embodiments, the storage device 150 may be directly connected to or communicate with one or more other components in the X-ray imaging system 100 (e.g., the processing device 140, the terminal 130). In some embodiments, the storage device 150 may be part of the processing device 140.

The description regarding the X-ray imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the processing device 140 and the X-ray imaging device 110 may be integrated into one single device. However, those variations and modifications do not depart the scope of the present disclosure.

FIG. 2 is a schematic diagram illustrating exemplary hardware and/or software components of an exemplary computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image data obtained from the X-ray imaging device 110, the terminal 130, the storage device 150, and/or any other component of the X-ray imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the X-ray imaging device 110, the terminal 130, the storage device 150, and/or any other component of the X-ray imaging system 100. In some embodiments, the storage 220 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for processing projection data or image data.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the X-ray imaging device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device on which the terminal 130 may be implemented according to some embodiments of the present disclosure.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android", Windows Phone", etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the X-ray imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of workstation or terminal device. A computer may also act as a server if appropriately programmed.

Figure 4:
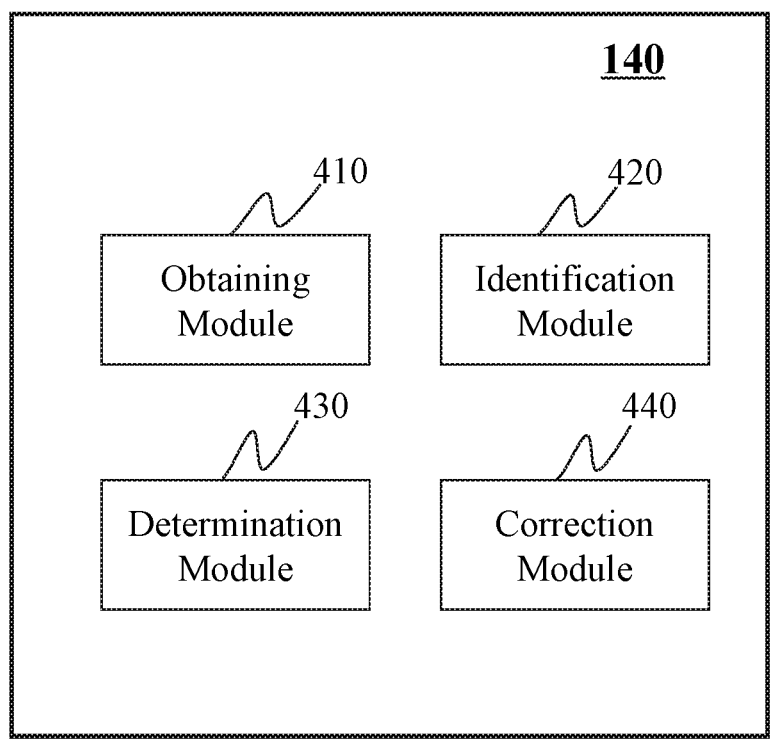
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an obtaining module 410, an identification module 420, a determination module 430, and a correction module 440.

The obtaining module 410 may be configured to obtain data and/or information related to the X-ray imaging system 100. Exemplary data and/or information obtained by the obtaining module 410 may include an image of a subject, scan data related to a scan, a reference image of air, a correction template, or the like, or any combination thereof. In some embodiments, the obtaining module 410 may obtain data and/or information related to the X-ray imaging system 100 from one or more components of the X-ray imaging system 100, such as the X-ray imaging device 110 and/or the storage device 150. Additionally or alternatively, the obtaining module 410 may obtain data and/or information related to the X-ray imaging system 100 from an external source via the network 120.

The identification module 420 may be configured to identify an OOI from the image of the subject. The OOI may include one or more pixels. An OOI may refer to any physical portion of the subject, such as an organ, a tissue, or the like, or any combination thereof. The "identifying an OOI from the image" may refer to "identifying a region in the image that corresponds to the OOI". In some embodiments, the identification module 420 may identify the OOI from the image by segmenting the OOI from the image. The OOI segmentation may be performed according to one or more image segmentation algorithms. More descriptions regarding the image segmentation may be found elsewhere in the present disclosure. See, e.g., operation 530 and the relevant descriptions thereof.

The determination module 430 may be configured to may determine an equivalent thickness of the OOI corresponding to a pixel of the OOI. The equivalent thickness of the OOI corresponding to the pixel may refer to a travelling distance of the radiation photon(s) corresponding to the pixel through the subject. In some embodiments, the equivalent thickness of the OOI corresponding to the pixel may be determined based on a pixel value (e.g., a grey value) of the pixel, a reference image of air, and/or the attenuation characteristic of the OOI. More descriptions regarding the determination of the equivalent thickness of the OOI corresponding to the pixel of the OOI may be found elsewhere in the present disclosure. See, e.g., operation 540 and the relevant descriptions thereof.

Additionally or alternatively, the determination module 430 may be configured to determine a scatter correction coefficient of the pixel based at least in part on the equivalent thickness of the OOI corresponding to the pixel. In some embodiment, the determination module 430 may determine the scatter correction coefficient of the pixel based on a correction template that corresponds to a target equivalent thickness. The target equivalent thickness may be the equivalent thickness of the OOI corresponding to the pixel. More descriptions regarding the determination of the scatter correction coefficient of the pixel may be found elsewhere in the present disclosure. See, e.g., operation 550 and the relevant descriptions thereof.

In some embodiments, the determination module 430 may be configured to generate a correction template based on photon information related to a scan of a phantom. The photon information may be related to a plurality of photons that are detected by the plurality of detector units of the X-ray imaging device 110 during the scan of the phantom. In some embodiments, the determination module 430 may generate a plurality of correction templates corresponding to different image conditions and/or different phantoms (e.g., different phantoms having different thicknesses and/or different attenuation characteristics). More descriptions regarding the generation of a correction template may be found elsewhere in the present disclosure. See, e.g., FIG. 8 and the relevant descriptions thereof.

The correction module 440 may be configured to correct the pixel value of a pixel using the corresponding scatter correction coefficient. In some embodiments, if the scatter correction coefficient of a pixel is a primary ratio, the correction module 440 may correct the pixel by multiplying its pixel value (e.g., grey value) by the primary ratio. In some embodiments, if the scatter correction coefficient of the pixel is a scatter ratio, the correction module 440 may correct the pixel by multiplying its pixel value (e.g., grey value) by the difference between 1 and the scatter ratio.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, the processing device 140 may include one or more other modules. Additionally or alternatively, one or more modules of the processing device 140 described above may be omitted. For example, the processing device 140 may include a storage module to store data generated by the modules in the processing device 140. As another example, the processing device 140 may include a generation module configured to generate one or more correction templates. In some embodiments, a module of the processing device 140 may be divided into two or more sub-modules.

Figure 5:
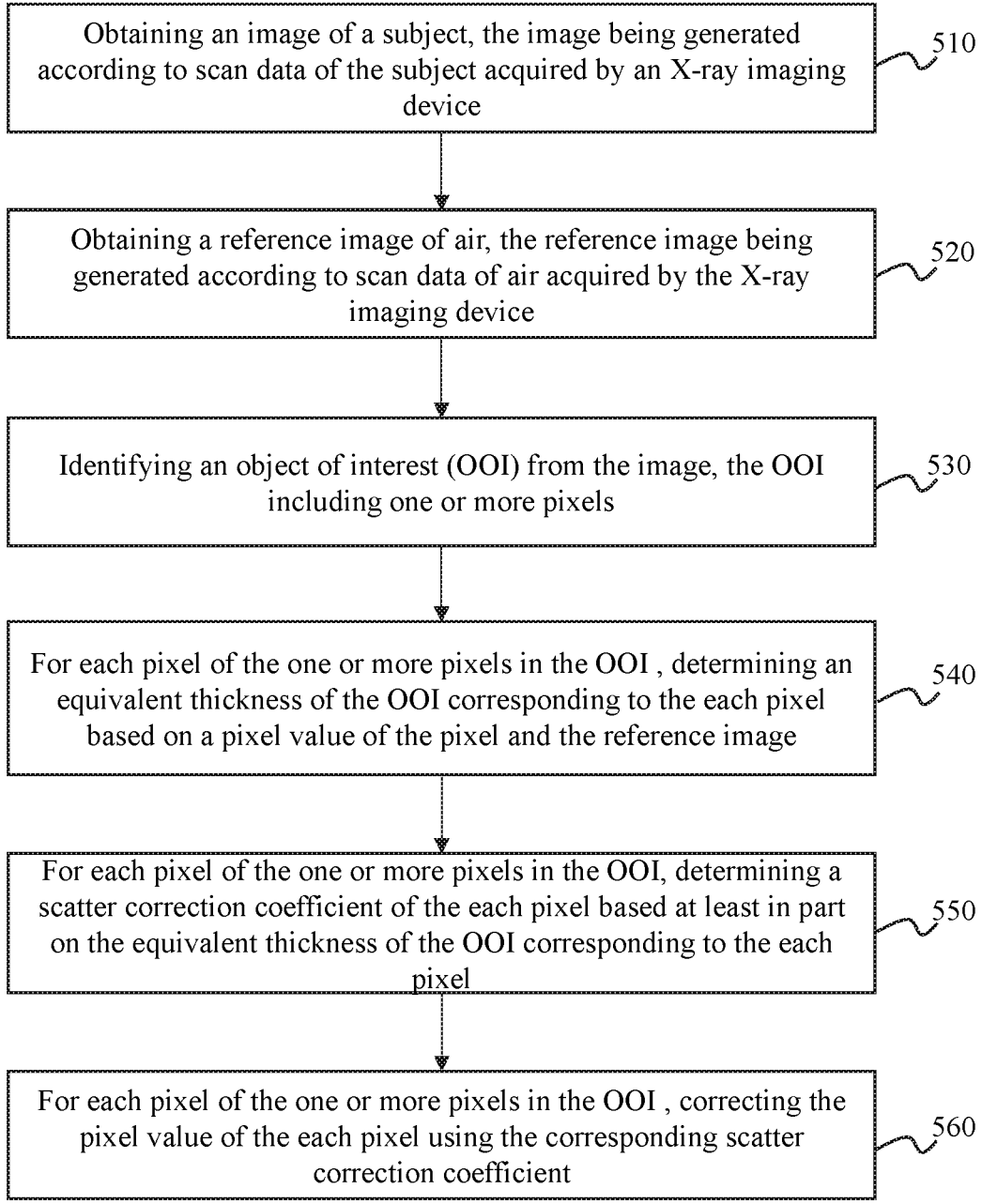
FIG. 5 is a flowchart illustrating an exemplary process for scatter correction of an image according to some embodiments of the present disclosure.

FIG. 5 is a flowchart illustrating an exemplary process for scatter correction of an image according to some embodiments of the present disclosure. In some embodiments, one or more operations of process 500 illustrated in FIG. 5 may be implemented in the X-ray imaging system 100 illustrated in FIG. 1. For example, the process 500 illustrated in FIG. 5 may be stored in a storage device of the X-ray imaging system 100 (e.g., the storage device 150, the storage 220, the storage 390) in the form of instructions, and invoked and/or executed by the processing device 140 (implemented in, for example, the processor 210 of the computing device 200 as illustrated in FIG. 2) or the terminal 130 (implemented in, for example, the CPU 340 of the mobile device 300 as illustrated in FIG. 3).

In 510, the obtaining module 410 may obtain an image of a subject. The image may be generated according to scan data of the subject acquired by the X-ray imaging device 110.

The subject may be biological or non-biological. Merely by way of example, the subject may include a patient, an organ of the patient, a tissue of the patient, or any body part of the patient, or any combination thereof. As another example, the subject may be a man-made subject, such as a water phantom, a phantom of a human organ or tissue.

In some embodiments, the X-ray imaging device 110 may be operated to perform a scan on the subject to generate the scan data of the subject. During the scan of the subject, the radiation source 115 may emit X-ray photons toward the subject. At least a portion of the radiation photons may directly pass through the subject, be absorbed by the subject, or be scattered by the subject. As used herein, a radiation photon directly passing through the subject may be referred to as a primary photon, and a radiation photon scattered by the subject may be referred to as a scattered photon. The primary photon(s) as well as the scattered photon(s) passing through the subject may be detected by a plurality of detector units of the X-ray imaging device 110. Each of the detector units may collect a portion of the scan data of the subject in response to the detected radiation photons. The portion of the scan data collected by a detector unit may be used to determine a pixel value (e.g., grey value) of a pixel in the image of the subject. For convenience of description, a pixel may be regarded as being corresponding to the detector unit acquiring the portion of the scan data that corresponds to the pixel, and being corresponding to the radiation photons detected by the corresponding detector unit. In some embodiments, the X-ray imaging device 110 may be operated without a grid during the acquisition of the scan data of the subject.

In some embodiments, the scan of the subject may be performed by the X-ray imaging device 110 under a target imaging condition. The target imaging condition may be prescribed by one or more imaging parameters, such as a size of a field of view (FOV) of the X-ray imaging device 110, a distance between the subject and the detector 112, a distance between the subject and the radiation source 115, a distance between the detector 112 and the radiation source 115, a radiation dose, a scanning time, a tube voltage, a tube current, or the like, or any combination thereof. In some embodiments, during the scan of the subject, a tube of the X-ray imaging device 110 may emit a cone beam toward the subject. In some embodiments, the cone beam may be collimated by a collimator into a rectangular beam, for example, before passing through the subject. The rectangular beam may irradiate on the detector 112. The size of the irradiation area of the rectangular beam on the detector 112 (or the projection of the rectangular beam on the detector 112) may be referred to as the size of the FOV of the X-ray imaging device 110.

In some embodiments, the image of the subject may be a 2D image, such as an X-ray image generated by a DR imaging device, or a slice image generated by a CT imaging device. In some embodiments, the image of the subject may be obtained by the obtaining module 410 from one or more components of the X-ray imaging system 100, such as the X-ray imaging device 110, the storage device 150, and/or the storage 220. Additionally or alternatively, the image of the subject may be obtained by the obtaining module 410 from an external source (e.g., a medical database) via the network 120.

In 520, the obtaining module 410 may obtain a reference image of air. The reference image may be generated according to scan data of air acquired by the X-ray imaging device 110.

In some embodiments, the X-ray imaging device 110 may be operated to perform a scan of air to generate the scan data of air. Optionally, the scan of air may be performed under the same imaging condition as the scan of the subject as described in connection with operation 510. In some embodiments, the obtaining module 410 may obtain the reference image of air from the X-ray imaging device 110 or an external source (e.g., a medical database) via the network 120. Alternatively, the reference image may be previously generated and stored in a storage device of the X-ray imaging system 100, such as the storage device 150 and/or the storage 220. The obtaining module 410 may access the storage device and obtain the reference image of air stored therein. For example, the X-ray imaging device 110 may be operated to perform a plurality of scans of air under different imaging conditions (e.g., under different FOV of the X-ray imaging device 110, different distances between the radiation source 115 and the detector 112) to generate scan data of air corresponding to the different imaging conditions. The processing device 140 and/or another computing device may generate a plurality of reference images of air corresponding to the different imaging conditions, and store the reference images corresponding to the different imaging conditions in the storage device of the X-ray imaging system 100. In 520, the obtaining module 410 may access the storage device and obtain the reference image of air that is generated under the same imaging condition as the target imaging condition.

In 530, the identification module 420 may identify an OOI from the image of the subject. The OOI may include one or more pixels.

As used herein, an OOI may refer to any physical portion of the subject, such as an organ, a tissue, or the like, or any combination thereof. The "identifying an OOI from the image" may refer to "identifying a region in the image that corresponds to the OOI". Additionally, for illustration purposes, an OOI may also refer to a region of the image that corresponds to physical portion(s) of the subject. Exemplary organs of the subject may include the heart, the brain, a lung, the cardiac, the stomach, the spleen, or the like. Exemplary tissues of the subject may include adipose tissue, connective tissue, nerve tissue, epithelial tissue, muscle tissue, bone and skeletal tissue, or the like, or any combination thereof. In some embodiments, the identified OOI may include a single type of organ or tissue. Normally, different types of organs and/or tissues of the subject may have different attenuation characteristics. The attenuation characteristic of an organ or tissue may be represented by, for example, a linear attenuation coefficient, a mass attenuation coefficient, a CT value, or the like, or any combination thereof. Accordingly, in some embodiments, different types of organs and/or tissues may need to be corrected, respectively, by considering their attenuation characteristics.

In some embodiments, the identification module 420 may identify an OOI from the image of the subject by segmenting the OOI from the image of the subject. The segmentation of the OOI may be performed according to one or more image segmentation algorithms. Exemplary image segmentation algorithms may include a threshold-based segmentation algorithm, an edge-based segmentation algorithm, a region-based segmentation algorithm, a clustering-based algorithm, an image segmentation algorithm based on wavelet transform, an image segmentation algorithm based on mathematical morphology, and an image segmentation algorithm based on artificial neural network, or the like, or any combination thereof.

In some embodiment, the identification module 420 may obtain position information of each pixel of the OOI in the image in the identification of the OOI. Merely by way of example, the image may be represented by a matrix. The matrix may include a plurality of elements each of which corresponds to a pixel in the image. The position of a pixel of the OOI may be represented by the position of the corresponding element in the matrix, such as the $N^{th}$ row and the $M^{th}$ column in the matrix. N and M may have any positive value.

In 540, for each of the one or more pixels in the OOI, the determination module 430 may determine an equivalent thickness of the OOI corresponding to the pixel based on a pixel value of the pixel and the reference image.

As used herein, the equivalent thickness of the OOI corresponding to a pixel may refer to a travelling distance of the radiation photon(s) corresponding to the pixel through the subject. The travelling distance of the corresponding radiation photon(s), and/or the characteristic (e.g., the attenuation characteristic, the density) of the OOI may affect the attenuation of the radiation photon(s) during the scan of the subject, which in turn may affect the pixel value (e.g., grey value) of the pixel in the image of the subject. Accordingly, the equivalent thickness of the OOI corresponding to the pixel and/or the characteristic of the OOI may need to be considered in the correction of the pixel value of the pixel.

In some embodiments, the equivalent thickness of the OOI corresponding to the pixel may be determined based on the pixel value (e.g., grey value) of the pixel, the reference image, and/or the attenuation characteristic of the OOI. More descriptions regarding the determination of the equivalent thickness of the OOI corresponding to each pixel of the OOI may be found elsewhere in the present disclosure. See, e.g., FIG. 6 and the relevant descriptions thereof.

In 550, for each of the one or more pixels in the OOI, the determination module 430 may determine a scatter correction coefficient of the pixel based at least in part on the equivalent thickness of the OOI corresponding to the pixel.

As described in connection with operation 510, the pixel value (e.g., grey value) of a pixel may be affected by the primary photons and/or the scattered photons that are detected by the detector unit corresponding to the pixel. A scatter correction coefficient of the pixel may be used to reduce or eliminate the effect of the scattered photons on the pixel value (e.g., grey value) of the pixel.

In some embodiment, in order to determine a scatter correction coefficient of a pixel, the determination module 430 may obtain a correction template that corresponds to a target equivalent thickness. The target equivalent thickness may be the equivalent thickness of the OOI corresponding to the pixel. As used in the present disclosure, a first value may be considered as being substantially equal to a second value if the difference between the first value and the second value is within a certain range, for example, ±0.1%, ±1%, ±5%, or ±10% of the second value, unless otherwise stated. The correction template may include a plurality of scatter correction coefficients corresponding to the plurality of detector units of the X-ray imaging device 110. Each scatter correction coefficient may correspond to one of the detector units and be used to correct the pixel value (e.g., grey value) of the pixel corresponding to the detector unit. The scatter correction coefficient corresponding to a detector unit may include, for example, a scatter-to-primary ratio (SPR), a scatter ratio, a primary ratio, or any other coefficient for scatter correction. For example, a detector unit may detect a plurality of photons (including scattered photons and/or primary photons) during a scan. The scatter ratio may refer to a ratio of the photon energy of the detected scattered photons to the total photon energy of the detected photons. The primary ratio may refer to a ratio of the photon energy of the detected primary photons to the total photon energy of the detected photons. The SPR may refer to a ratio of the photon energy of the detected scattered photons to the photon energy of the detected primary photons. For a detector unit, the corresponding primary ratio may be equal to the difference between 1 and the corresponding scatter ratio, and the corresponding SPR may be equal to the quotient of the corresponding scatter ratio and the corresponding primary ratio. In some embodiments, different detector units may correspond to the same type or different types of scatter correction coefficients.

In some embodiments, the determination module 430 may determine a scatter correction coefficient of a pixel by considering one or more other factors in addition to the equivalent thickness of the OOI corresponding to the pixel. Merely by way of example, because the attenuation of X-ray photons during the scan of the subject may also be affected by the attenuation characteristic of the OOI and/or the target imaging condition. The determination module 430 may determine the scatter correction coefficient of the pixel based on the attenuation characteristic of the OOI and/or the target imaging condition of the scan of the subject. For example, the determination module 430 may determine the scatter correction coefficient of the pixel by looking up a correction template generated based on a phantom having a substantially similar attenuation characteristic to the OOI. Additionally or alternatively, the determination module 430 may determine the scatter correction coefficient of the pixel by looking up a correction template generated under the same imaging condition as the target imaging condition. More descriptions regarding the correction template and the determination of a scatter correction coefficient corresponding to a pixel may be found elsewhere in the present disclosure. See, e.g., FIGS. 7 and 8 and the relevant descriptions thereof.

In 560, for each of the one or more pixels in the OOI, the correction module 440 may correct the pixel value of the pixel using the corresponding scatter correction coefficient.

In some embodiments, if the scatter correction coefficient of a pixel is a primary ratio, the correction module 440 may correct the pixel by multiplying its pixel value (e.g., grey value) by the primary ratio. In some embodiments, if the scatter correction coefficient of the pixel is a scatter ratio, the correction module 440 may correct the pixel by multiplying its pixel value (e.g., grey value) by the difference between 1 and the scatter ratio.

It should be noted that descriptions regarding the process 500 is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. In some embodiments, one or more operations of the process 500 may be omitted and/or one or more additional operations may be added. For example, the identification module 420 may identify a plurality of OOIs from the image. The plurality of OOIs may include different organs and/or tissues of the subject and each OOI may include one or more pixels. For each of the OOIs, the processing device 140 may perform operations 540 to 560 to correct the pixel value(s) of the pixel(s) in the each OOI. The processing device 140 may further generate a corrected image by combining the plurality of corrected OOIs. In some embodiments, the combination of the corrected OOIs may be performed based on the position information of each OOI in the image. In some embodiments, the operations of the process 500 may be performed in any suitable order. Merely by way of example, operations 510 and 520 may be performed simultaneously, or operation 520 may be performed before operation 510.

In some embodiments, for a 3D CT image including one or more slice images, the processing device 140 may perform the process 500 for each slice image to correct the each slice image. The processing device 140 may then generate a corrected 3D CT image by merging the corrected slice images.

Figure 6:
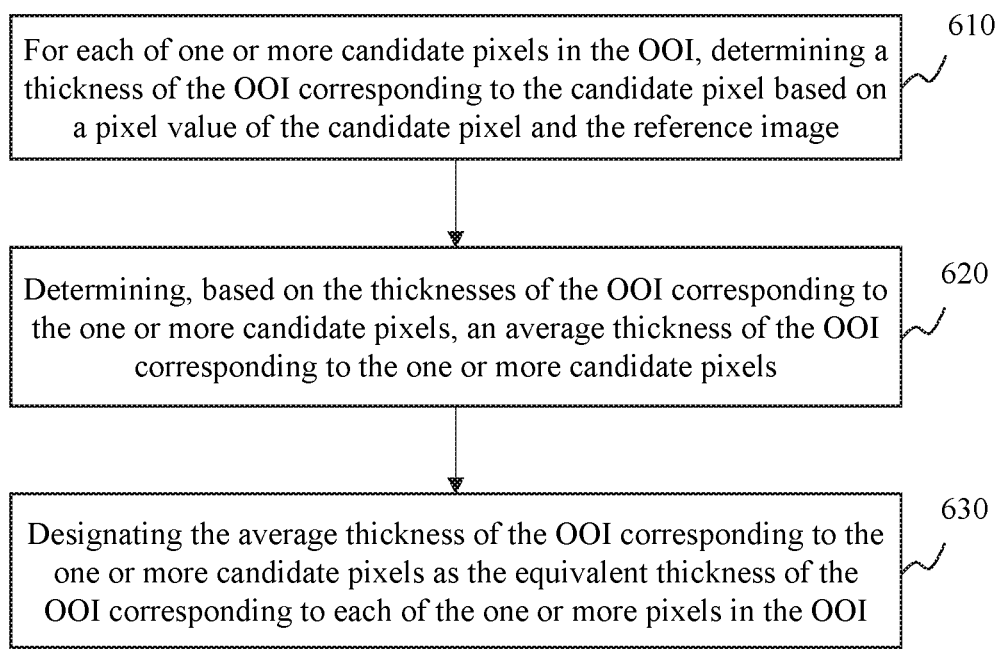
FIG. 6 is a flowchart illustrating an exemplary process for determining an equivalent thickness of an OOI according to some embodiments of the present disclosure.

FIG. 6 is a flowchart illustrating an exemplary process for determining an equivalent thickness of an OOI corresponding to a pixel according to some embodiments of the present disclosure. In some embodiments, one or more operations of process 600 illustrated in FIG. 6 may be implemented in the X-ray imaging system 100 illustrated in FIG. 1. For example, the process 600 illustrated in FIG. 6 may be stored in a storage device of the X-ray imaging system 100 (e.g., the storage device 150, the storage 220, the storage 390) in the form of instructions, and invoked and/or executed by the processing device 140 (implemented in, for example, the processor 210 of the computing device 200 as illustrated in FIG. 2) or the terminal 130 (implemented in, for example, the CPU 340 of the mobile device 300 as illustrated in FIG. 3). In some embodiments, part or all of the process 600 may be performed to achieve operation 540 in the process 500.

In 610, for each of one or more candidate pixels in the OOI, the determination module 430 may determine a thickness of the OOI corresponding to the candidate pixel based on a pixel value of the candidate pixel and the reference image.

A candidate pixel may be any pixel of the OOI. In some embodiments, the candidate pixel(s) may be the whole pixel(s) of the OOI or a selected portion of the pixel(s) of the OOI. In some embodiments, the thickness of the OOI corresponding to a candidate pixel in the OOI may be determined according to Equation (1) as below:

$$L_1 = \ln\left(\frac{I_0}{I_1}\right)/mv1, \qquad (1)$$

where $L_1$ refers to the thickness of the OOI corresponding to the candidate pixel, $I_0$ refers to the pixel value (e.g., the grey value) of a pixel in the reference image corresponding to the candidate pixel, $I_1$ refers to the pixel value (e.g., the grey value) of the candidate pixel in the image of the subject, and mv1 refers to a linear attenuation coefficient of the OOI. As used herein, a pixel in the reference image corresponding to the candidate pixel may refer to a pixel located at the same position in the reference image as the position of the candidate pixel in the image of the subject. The linear attenuation coefficient of the OOI may relate to the organ or tissue type of the OOI. In some embodiments, different OOIs with different organ or tissue types may have different linear attenuation coefficients. In some embodiments, the linear attenuation coefficient of the OOI may be determined by looking up a table recording the linear attenuation coefficients of different substances (e.g., organs and/or tissues). It should be noted that the Equation (1) above is merely provided for illustration purposes, and not intended to limit the scope of the present disclosure. For persons having ordinary skills in the art, various modifications and changes may occur, and those variations and modifications also fall within the scope of the present disclosure. Merely by way of example, the linear attenuation coefficient may be replaced by, for example, a product of a mass attenuation coefficient of the OOI and a density of the OOI.

In 620, the determination module 430 may determine an average thickness of the OOI corresponding to the candidate pixel(s) based on the thicknesses of the OOI corresponding to the candidate pixel(s). The average thickness of the OOI corresponding to the candidate pixel(s) in the OOI may be determined by dividing the sum of the thicknesses of the OOI corresponding to the candidate pixel(s) by the total number of the candidate pixel(s).

In 630, the determination module 430 may designate the average thickness of the OOI corresponding to the candidate pixel(s) as the equivalent thickness of the OOI corresponding to each of the pixel(s) in the OOI.

In some embodiments, before operation 610, the identification module 420 may segment or divide the OOI into a plurality of sub-areas, each of which includes one or more pixels. The number of pixels in different sub-areas may be the same or different. Different sub-areas may have different shapes and/or sizes. The determination module 430 may determine the equivalent thickness of the OOI corresponding to the pixel(s) in different sub-areas, respectively, because the thicknesses of different portions of the OOI may be different. In some embodiments, the determination module 430 may perform operations similar to operations 610 to 630 for each of the sub-areas. For one or more candidate pixels in each sub-area, the determination module 430 may determine the thickness of the OOI corresponding to each candidate pixel in the sub-area. The determination module 430 may then determine an average thickness of the sub-area corresponding to the candidate pixel(s) in the sub-area, and designate the average thickness of the sub-area corresponding to the candidate pixel(s) in the sub-area as the equivalent thickness of the OOI corresponding to each pixel in the sub-area.

It should be noted that descriptions regarding the process 600 is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, in operation 620, the determination module 430 may determine another parameter (e.g., a median thickness, or a mode thickness) for measuring the thickness of the OOI corresponding to the candidate pixel(s) in the OOI. In 630, the parameter may be designated as the equivalent thickness of the OOI corresponding to each pixel in the OOI.

FIG. 7 is a flowchart illustrating an exemplary process for determining a scatter correction coefficient of a pixel according to some embodiments of the present disclosure. In some embodiments, one or more operations of process 700 illustrated in FIG. 7 may be implemented in the X-ray imaging system 100 illustrated in FIG. 1. For example, the process 700 illustrated in FIG. 7 may be stored in a storage device of the X-ray imaging system 100 (e.g., the storage device 150, the storage 220, the storage 390) in the form of instructions, and invoked and/or executed by the processing device 140 (implemented in, for example, the processor 210 of the computing device 200 as illustrated in FIG. 2) or the terminal 130 (implemented in, for example, the CPU 340 of the mobile device 300 as illustrated in FIG. 3).

In some embodiments, part or all of the process 700 may be performed to achieve operation 550 in the process 500. For example, the processing device 140 may perform the process 700 for each pixel of the one or more pixels of the OOI to determine the equivalent thickness of the OOI corresponding to the each pixel. For brevity and illustration purposes, the implementation of the process 700 for one pixel (e.g., any one of the pixel(s) of the OOI) is described as an example.

In 710, the obtaining module 410 may obtain a correction template that corresponds to a target equivalent thickness. The target equivalent thickness may be the equivalent thickness of the OOI corresponding to the pixel. The correction template may include a plurality of scatter correction coefficients corresponding to the plurality of detector units of the X-ray imaging device 110. In some embodiments, the correction template may be stored in various forms in a storage device of the X-ray imaging system 100 (e.g., the storage device 150). For example, the correction template may be denoted in the form of a table recording the identifications (or coordinates) of the detector units and their corresponding scatter correction coefficients. As another example, the correction template may be denoted in the form of a map (or a matrix). Different positions of the map (or matrix) may represent different detector units, and each position may record the scatter correction coefficient of the corresponding detector unit.

In some embodiments, the correction template corresponding to the target equivalent thickness may be generated based on a scan of a phantom. The thickness of the phantom may be equal to or substantially equal to the target equivalent thickness. As used herein, the thickness of a phantom may refer to the thickness along the direction between the radiation source 115 and the detector 112. In some embodiments, the phantom may have a uniform or a substantially uniform thickness along the direction between the radiation source 115 and the detector 112. Additionally or alternatively, the attenuation characteristic(s) of the phantom may be similar to, equal to or substantially equal to the attenuation characteristic(s) of the OOI. In some embodiments, the correction template corresponding to corresponding to the target equivalent thickness may be generated according to a correction template generation process as described in connection with FIG. 8.

In some embodiments, the correction template corresponding to the target equivalent thickness may be previously generated and stored in a storage device (e.g., the storage device 150 and/or the storage 220) of the X-ray imaging system 100. The obtaining module 410 may access the storage device and obtain the correction template corresponding to the target equivalent thickness stored therein. For example, the X-ray imaging device 110 may be operated to perform one or more scans of one or more phantoms. The phantoms may have one or more thicknesses. For example, a first phantom may have a first thickness, and a second phantom may have a second thickness different from the first thickness. In some embodiments, the thickness(es) of the phantoms may have values in a certain range such that each equivalent thickness of the OOI may correspond to a phantom having a thickness that is substantially equal to the each equivalent thickness of the OOI. Based on the scan(s) of the phantom(s) having the thickness(es), the processing device 140 or another computing device may generate one or more correction templates corresponding to the thickness(s), and store the correction template(s) in a storage device of the X-ray imaging system 100. In 710, the obtaining module 410 may access the storage device and obtain the correction template generated based on a phantom having a thickness that is substantially equal to the target equivalent thickness.

In some embodiments, the scan of the subject may be performed under a target imaging condition as described in connection with operation 510. The target imaging condition may be considered in obtaining the correction template corresponding to the target equivalent thickness. For example, the obtaining module 410 may obtain a plurality of candidate correction templates corresponding to the target equivalent thickness. Each of the candidate correction templates may correspond to an imaging condition and be generated according to a scan of one or more phantoms under the corresponding imaging condition. The phantom(s) may have a thickness being equal to or substantially equal to the target equivalent thickness. Additionally or alternatively, the phantom(s) may have the same or substantially same attenuation characteristic as the OOI. In some embodiments, the candidate correction templates may be generated by performing one or more operations of process 900 as described in connection with FIG. 9, and be stored in a storage device (e.g., the storage device 150 and/or the storage 220) of the X-ray imaging system 100. The obtaining module 410 may access the storage device and obtain the candidate correction templates stored therein.

After the candidate correction templates are obtained, the determination module 430 may then select a candidate correction template corresponding to the target imaging condition among the candidate correction templates. The selected candidate correction template may be designated as the correction template corresponding to the target equivalent thickness. The selection may be performed according to one or more imaging parameters that prescribe the imaging condition and the target imaging condition. For example, if a candidate correction template is generated under the same imaging parameters as the target imaging condition, it may be selected as the correction template corresponding to the target equivalent thickness. As another example, the determination module 430 may compare the target imaging condition with the imaging condition corresponding to each candidate correction template, for example, by comparing the values of the imaging parameter(s). The determination module 430 may then select the candidate correction template whose corresponding imaging condition has the smallest difference with the target imaging condition, and designate the selected candidate correction template as the correction template corresponding to the target equivalent thickness.

In 720, the determination module 430 may designate, in the obtained correction template, a scatter correction coefficient of the detector unit acquiring a portion of the scan data that corresponds to the pixel as the scatter correction coefficient of the pixel. As described in connection with FIG. 5, the portion of the scan data corresponding to the pixel may be acquired by a detector unit. The pixel value of the pixel may be corrected based on the scatter correction coefficient of the corresponding detector unit. In some embodiments, the determination module 430 may first identify the detector unit that corresponds to the pixel, and then determine the corresponding scatter correction coefficient by, for example, looking up a table or map denoting the correction template.

FIG. 8 is a flowchart illustrating an exemplary process for generating a correction template corresponding to a target equivalent thickness according to some embodiments of the present disclosure. In some embodiments, one or more operations of process 800 illustrated in FIG. 8 may be implemented in the X-ray imaging system 100 illustrated in FIG. 1. For example, the process 800 illustrated in FIG. 8 may be stored in a storage device of the X-ray imaging system 100 (e.g., the storage device 150, the storage 220, the storage 390) in the form of instructions, and invoked and/or executed by the processing device 140 (implemented in, for example, the processor 210 of the computing device 200 as illustrated in FIG. 2) or the terminal 130 (implemented in, for example, the CPU 340 of the mobile device 300 as illustrated in FIG. 3). In some embodiments, the generated correction template corresponding to the target equivalent thickness may be used in operation 550 to determine a scatter correction coefficient of a pixel. The target equivalent thickness may be the equivalent thickness of the OOI corresponding to the pixel as described in connection with operation 550. In some embodiments, part or all of the process 800 may be performed to achieve operation 710 in the process 700.

In 810, the obtaining module 410 may obtain photon information related to a scan of a phantom. The photon information may be related to a plurality of photons that are detected by the plurality of detector units of the X-ray imaging device 110 during the scan of the phantom. The phantom may have a thickness being equal to or substantially equal to the target equivalent thickness. Additionally or alternatively, the phantom may have an attenuation characteristic equal to or substantially equal to an attenuation characteristic of the OOI. Merely by way of example, if the OOI is a lung and the target equivalent thickness is 10 cm, the photon information obtained in operation 810 may be related to a scan of a phantom that has a thickness of 10 cm and a substantially similar attenuation characteristic to the lung. In some embodiments, the phantom may be a water phantom, a polymethyl methacrlyate (PMMA) phantom, or any other type of phantom. The phantom may have any suitable shape and/or size. In some embodiments, the size of the phantom may be greater than that of the OOI. Additionally or alternatively, the phantom may have a uniform or substantially uniform thickness along the direction between the radiation source 115 and the detector 112.

The photon information related to the photons may include an incidence angle of each photon on the plurality of detector units and a photon energy of each photon. The incidence angle of a photon on the detector units may refer to an angle between the trajectory of the photon and the detector plane formed by the detector units. In some embodiments, the photon information may be obtained based on a Monte-Carlo simulation technique. For example, the Monte-Carlo simulation technique may simulate the scan of the phantom by building a probability distribution model according to a physical property (e.g., an attenuation characteristic) of the phantom and/or a geometry of an imaging system (e.g., the X-ray imaging system 100) in which the scan is performed. The probability distribution model may be used to estimate the interaction between the phantom and photons emitted by a radiation source, the trajectory of the photons during the scan, and one or more parameters (e.g., the incidence angle and/or the photon energy) related to the photons. In some embodiments, the scan of the phantom may be simulated by Monte Carlo software, such as a software toolkit EGSnrc or Geant4.

In 820, the determination module 430 may identify, based on the photon information, one or more scattered photons among the plurality of photons.

In some embodiments, the scattered photon(s) may be identified based on the incidence angles of the photons, the positions of the detector units, and/or the position of the radiation source 115. For example, for a photon, the detector plane and a line connecting the radiation source 115 and the detector unit that detects the photon may form an angle, and the incidence angle may be compared with the formed angle. If the incidence angle of the photon is not equal to the formed angle, it can be speculated that the photon is deflected and/or scattered when passing through the phantom. If the incidence angle of the photon is equal to the formed angle, it can be speculated that the photon directly passes through the phantom without being scattered. Additionally or alternatively, the scattered photon(s) may be identified based on the simulated trajectory of the photons as described in connection with operation 810. If a photon is deflected when passing through the phantom, it may be identified as a scattered photon. If a photon passes through the phantom directly without being deflected, it may be identified as a primary photon.

In 830, the determination module 430 may determine the plurality of scatter correction coefficients corresponding to the plurality of detector units based on the photon information and the identified one or more scattered photons.

As described in connection with operation 550, the scatter correction coefficient corresponding to a detector unit may include, for example, an SPR, a scatter ratio, a primary ratio, or the like. For each detector unit, the determination module 430 may determine the corresponding scatter correction coefficient based on the type and photon energy of the photon(s) detected by the detector unit. Taking the primary ratio of a detector unit as an example, the determination module 430 may determine a total photon energy of the primary photons detected by the detector unit and a total photon energy of all the photons (including the primary and scattered photons) detected by the detector unit, and then divide the total photon energy of the primary photons by the total energy of all photons. In some embodiments, different detector units may correspond to the same or different scatter correction coefficients. In some embodiments, different sets of scatter correction coefficients for the detector units may be determined for phantoms with different thicknesses.

It should be noted that descriptions regarding the process 800 is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. In some embodiments, the process 800 may be performed by a computing device other than the processing device 140. In some embodiments, the scan of the subject in operation 510 may be performed under a target imaging condition. The scan of the phantom in operation 810 may also be performed under the target imaging condition in order to generate the correction template corresponding to the target imaging condition. In some embodiments, the scan of the phantom may be performed before the scan of the subject. For example, one or more scans of one or more phantoms may be performed before the scan of the subject. The phantom(s) may have one or more thicknesses. Additionally or alternatively, the scan(s) may be performed under one or more imaging conditions. As such, one or more correction templates corresponding to the thickness(s) and/or imaging condition(s) may be generated, and stored in a storage device (e.g., the storage device 150 and/or the storage 220) of the X-ray imaging system 100. In scatter correction, the processing device 140 (e.g., the obtaining module 410) may access the storage device and obtain, from the storage device, a suitable correction template among the previously generated correction template(s).

In some embodiments, the scatter correction coefficients corresponding to the detector units may be determined by performing a first scan and a second scan on a same phantom. The first scan may be performed by the X-ray imaging device 110 on the phantom, and a first photon energy detected by each detector unit in the first scan may be measured by a meter. The second scan may be performed when a blocking device is placed between the phantom and the detector 112 of the X-ray imaging device 110. A second photon energy detected by each detector unit in the second scan may be measured by the meter. The blocking device may be made of a special material (e.g., lead), and configured to completely or partially block the scattered photons passing through the phantom during the second scan. The first photon energy detected by a detector unit may be a total photon energy of the primary photons and scattered photons detected by the detector unit. The second photon energy detected by a detector unit may be a total photon energy of the primary photons detected by the detector unit. Accordingly, the processing device 140 may determine a primary ratio corresponding to a detector unit by dividing the second photon energy of the detector unit by the first photon energy of the detector unit.

FIG. 9 is a flowchart illustrating an exemplary process for determining a plurality of correction templates corresponding to different imaging conditions according to some embodiments of the present disclosure. In some embodiments, one or more operations of process 900 illustrated in FIG. 9 may be implemented in the X-ray imaging system 100 illustrated in FIG. 1. For example, the process 900 illustrated in FIG. 9 may be stored in a storage device of the X-ray imaging system 100 (e.g., the storage device 150, the storage 220, the storage 390) in the form of instructions, and invoked and/or executed by the processing device 140 (implemented in, for example, the processor 210 of the computing device 200 as illustrated in FIG. 2) or the terminal 130 (implemented in, for example, the CPU 340 of the mobile device 300 as illustrated in FIG. 3).

In 910, the obtaining module 410 may obtain photon information related to a plurality of scans. Each of the plurality of scans may be performed on a phantom under an imaging condition. The imaging condition of a scan may be prescribed by one or more imaging parameters, such as a size of a FOV of the X-ray imaging device 110, a distance between the phantom and the detector 112, a distance between the phantom and the radiation source 115, a distance between the detector 112 and the radiation source 115, a radiation dose, a scanning time, a tube voltage, a tube current, or the like, or any combination thereof. The photon information of a scan may be related to a plurality of photons detected by a plurality of detector units of an X-ray imaging device 110 during the scan of the corresponding phantom. The photon information may include an incidence angle of each of the plurality of photons on the detector units and a photon energy of each photon.

In some embodiments, the plurality of scans may be performed in different imaging conditions so that a plurality of candidate correction templates corresponding to different imaging conditions may be generated based on the photon information related to the scans. A candidate correction template corresponding to a certain imaging condition may be used in the scatter correction of an image that is acquired under the same or substantially same imaging condition as the certain imaging condition. In some embodiments, the plurality of scans may be performed under different imaging conditions (e.g., different FOVs of the X-ray imaging device 110 and/or different distances between the phantom and the detector 112) such that each imaging condition may correspond to an imaging condition under which a certain portion (e.g., an organ or tissue) of the subject is scanned.

Additionally or alternatively, the plurality of scans may be performed on different phantoms so that a plurality of candidate correction templates corresponding to different phantoms may be generated based on the photon information related to the scans. The different phantoms may include phantoms of different organs and/or tissues, phantoms having different thicknesses, or the like, or any combination thereof. A phantom of an organ or a tissue may have a similar or substantially similar characteristic (e.g., an attenuation characteristic, a density, and/or size) to the corresponding organ or tissue. Merely by way of example, the plurality of scans may be performed on a plurality of liver phantoms having different thickness, a plurality of cardiac phantoms having different thicknesses, a plurality of fat tissue phantoms having different thickness, or the like, or any combination thereof. In some embodiments, a candidate correction template corresponding to a certain organ or tissue may be used in the scatter correction of the certain organ or tissue in an image. A candidate correction template corresponding to a specific thickness of an organ or tissue may be used in the scatter correction of a pixel of the organ or tissue in an image, in which the corresponding equivalent thickness of the pixel may be equal to or substantially equal to the specific thickness.

In some embodiments, for each scan, the obtaining module 410 may obtain the corresponding photon information in a similar manner as described in connection with operation 810.

In 920, for each of the plurality of scans, the determination module 430 may identify one or more scattered photons among the corresponding photons detected by the detector units of the X-ray imaging device 110 based on the corresponding photon information. In some embodiments, for each scan, the determination module 430 may identify the scattered photon(s) from the photons detected in the scan in a similar manner as described in connection with operation 820.

In 930, for each of the plurality of scans, the determination module 430 may determine a candidate correction template corresponding to the imaging condition under which the scan is performed based on the corresponding photon information and the corresponding scattered photons. The candidate correction template corresponding to an imaging condition may include a plurality of scatter correction coefficients each of which may correspond to a detector unit. In some embodiments, for each scan, the determination module 430 may determine the scatter correction coefficients of the corresponding correction template in a similar manner as described in connection with operation 830.

In some embodiments, the plurality of candidate correction templates corresponding to different imaging conditions may be used in the scatter correction of an image. For example, the obtaining module 410 may obtain an image of a subject (e.g., an image of the subject as described in connection with operation 510). The image may be generated according to scan data of the subject acquired by the X-ray imaging device 110 under a target imaging condition. The determination module 430 may select the correction template corresponding to the target imaging condition among the plurality of candidate correction templates. More descriptions regarding the selection of the correction template corresponding to the target imaging condition may be found elsewhere in the present disclosure. See, e.g., operation 710 and the relevant descriptions thereof. Then the correction module 440 may correct at least a portion of the image using the correction template corresponding to the target imaging condition. For example, for at least one pixel in the image, the correction module 440 may identify a scatter correction coefficient of a detector unit corresponding to the at least one pixel from the correction template corresponding to the target imaging condition. The corresponding detector unit of the pixel may acquire the portion of the scan data that corresponds to the at least one pixel. The correction module 440 may further correct the pixel value of the at least one pixel using the identified scatter correction coefficient.

In some embodiments, different organs and/or tissues of a subject may be corrected, respectively, as described elsewhere in this disclosure (e.g., FIG. 5 and the relevant descriptions). The obtaining module 410 may obtain an image of a subject and a reference image of air. Both the image of the subject and the reference image may be generated according to scan data acquired by the X-ray imaging device 110 under a target imaging condition. The identification module 420 may identify an OOI (e.g., an organ and/or tissue) from the image of the subject. The OOI may include one or more pixels. For each of the one or more pixels in the OOI, the determination module 430 may determine an equivalent thickness of the OOI corresponding to the pixel based on a pixel value of the pixel and the reference image. The determination module 430 may further select a correction template among the plurality of candidate correction templates. The selected correction template may correspond to the target imaging condition, and be generated according to a scan of a phantom that has a thickness being equal or substantially equal to the equivalent thickness of the OOI corresponding to the pixel. The correction module 440 may correct the pixel value of the pixel using the corresponding correction template in, for example, a similar manner as described in connection with FIG. 8. For example, the correction module 440 may identify a scatter correction coefficient of the detector unit acquiring a portion of the scan data that corresponds to the pixel, and correct the pixel value of the pixel using the identified scatter correction coefficient.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A system, comprising:
   at least one storage device including a set of instructions for scatter correction of an image; and
   at least one processor configured to communicate with the at least one storage device, wherein when executing the set of instructions, the at least one processor is configured to direct the system to:
      obtain an image of a subject, the image being generated by operating an X-ray imaging device to perform a first scan on the subject;
      obtain a reference image of air, the reference image being generated by operating the X-ray imaging device to perform a second scan on the air;
      identify an object of interest (OOI) from the image, the OOI including one or more pixels;
      for each pixel of the one or more pixels of the OOI,
         determine, based on a pixel value of the each pixel and the reference image, an equivalent thickness of the OOI corresponding to the each pixel, the equivalent thickness of the OOI corresponding to the pixel being a travelling distance of radiation photon(s) corresponding to the pixel through the subject;
         determine a scatter correction coefficient of the each pixel based at least in part on the equivalent thickness of the OOI corresponding to the each pixel; and
         correct the pixel value of the each pixel using the corresponding scatter correction coefficient.

2. The system of claim 1, wherein to determine the equivalent thickness of the OOI corresponding to the each pixel, the at least one processor is further configured to direct the system to:
   for each candidate pixel of one or more candidate pixels in the OOI, determine a thickness of the OOI corresponding to the each candidate pixel based on a pixel value of the each candidate pixel and the reference image;
   determine, based on the thicknesses of the OOI corresponding to the one or more candidate pixels, an average thickness of the OOI corresponding to the one or more candidate pixels; and
   designate the average thickness of the OOI corresponding to the one or more candidate pixels as the equivalent thickness of the OOI corresponding to the each pixel.

3. The system of claim 2, wherein to determine a thickness of the OOI corresponding to the each candidate pixel based on a pixel value of the each candidate pixel and the reference image, the at least one processor is further configured to direct the system to:
   determine a ratio of the pixel value the each candidate pixel in the image of the subject to a pixel value of a pixel in the reference image corresponding the each candidate pixel; and
   determine the thickness of the OOI corresponding to the each candidate pixel based on the ratio and a linear attenuation coefficient of the OOI.

4. The system of claim 1, wherein to determine the equivalent thickness of the OOI corresponding to the each pixel, the at least one processor is further configured to direct the system to:
   identify the OOI into a plurality of sub-areas;
   for each of the sub-areas,
      for each candidate pixel of one or more candidate pixels in the sub-area, determine a thickness of the OOI corresponding to the each candidate pixel based on a pixel value of the each candidate pixel and the reference image;
      determine, based on the thicknesses of the OOI corresponding to the one or more candidate pixels in the sub-area, an average thickness of the sub-area corresponding to the one or more candidate pixels in the sub-area; and
      designate the average thickness of the sub-area corresponding to the one or more candidate pixels in the sub-area as the equivalent thickness of the OOI corresponding to each pixel in the sub-area.

5. The system of claim 1, wherein to determine, for each pixel of the one or more pixels of the OOI, a scatter correction coefficient of the each pixel based at least in part on the equivalent thickness of the OOI corresponding to the each pixel, the at least one processor is further configured to direct the system to:
   obtain a correction template that corresponds to a target equivalent thickness, the target equivalent thickness being the equivalent thickness of the OOI corresponding to the each pixel, the correction template including a plurality of scatter correction coefficients corresponding to a plurality of detector units of the X-ray imaging device; and
   designate the scatter correction coefficient of the detector unit acquiring a portion of the scan data that corresponds to the each pixel as the scatter correction coefficient of the each pixel.

6. The system of claim 5, wherein the correction template that corresponds to the target equivalent thickness is generated according to a correction template generation process comprising:
   obtaining photon information related to a scan of a phantom, the photon information being related to a plurality of photons that are detected by the plurality of detector units of the X-ray imaging device during the scan, the phantom having thickness being substantially equal to the target equivalent thickness, the phantom having an attenuation characteristic being substantially equal to an attenuation characteristic of the OOI, the photon information including an incidence angle of each of the plurality of photons on the plurality of detector units and a photon energy of each of the plurality of photons;
   identifying, based on the photon information, one or more scattered photons among the plurality of photons; and
   determining, based on the photon information and the identified one or more scattered photons, the plurality of scatter correction coefficients corresponding to the plurality of detector units.

7. The system of claim 6, wherein the correction template corresponding to the target equivalent thickness is generated according to a Monte-Carlo simulation technique.

8. The system of claim 5, wherein the scan data of the subject is acquired by the X-ray imaging device under a target imaging condition, and to obtain a correction template corresponding to the target equivalent thickness, the at least one processor is further configured to direct the system to:
  obtain a plurality of candidate correction templates corresponding to the target equivalent thickness, each of the candidate correction templates corresponding to an imaging condition; and
  select, among the plurality of candidate correction templates, the candidate correction template corresponding to the target imaging condition as the correction template corresponding to the target equivalent thickness.

9. The system of claim 1, wherein the at least one processor is configured to further direct the system to:
  identify a plurality of OOIs from the image, each of the OOI including one or more pixels;
  for each OOI of the plurality of OOIs,
    determine an equivalent thickness of the each OOI corresponding to each pixel in the each OOI based on a pixel value of the each pixel in the each OOI and the reference image;
    determine a scatter correction coefficient of the each pixel in the each OOI based at least in part on the equivalent thickness of the each OOI corresponding to the each pixel in the each OOI; and
    correct the pixel value of the each pixel in the each OOI using the corresponding scatter correction coefficient; and
  generate a corrected image by combining the plurality of corrected OOIs.

10. The system of claim 1, wherein a scatter correction coefficient includes at least one of a scatter-to-primary ratio (SPR), a scatter ratio, or a primary ratio.

* * * * *